United States Patent
Merk et al.

(10) Patent No.: US 6,787,009 B2
(45) Date of Patent: Sep. 7, 2004

(54) BIPOLAR QUASI-DIVIDED ELECTROLYSIS CELLS

(75) Inventors: Claudia Merk, Limburgerhof (DE); Martin Brudermüller, Mannheim (DE); Hermann Pütter, Neustadt (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 194 days.

(21) Appl. No.: 10/013,873

(22) Filed: Dec. 13, 2001

(65) Prior Publication Data

US 2002/0108852 A1 Aug. 15, 2002

(30) Foreign Application Priority Data

Dec. 19, 2000 (DE) ......................... 100 63 195

(51) Int. Cl.⁷ ................... C25B 9/00; C25B 11/02; C25B 11/03
(52) U.S. Cl. ..................................... 204/268
(58) Field of Search ......................... 204/268

(56) References Cited

U.S. PATENT DOCUMENTS

| | | |
|---|---|---|
| 3,441,495 A | 4/1969 | Colman |
| 4,284,825 A | 8/1981 | Degner et al. |
| 4,539,081 A | 9/1985 | Degner et al. |
| 5,266,171 A | 11/1993 | Hermeling et al. |
| 6,077,414 A | 6/2000 | Pütter et al. |
| 6,242,653 B1 * | 6/2001 | Aquila et al. ............ 568/344 |

FOREIGN PATENT DOCUMENTS

| | | |
|---|---|---|
| DE | 28 48 397 A1 | 5/1980 |
| DE | 38 16 380 | 11/1989 |
| DE | 195 33 773 A1 | 3/1997 |
| EP | 0 129 795 | 1/1985 |
| EP | 0 460 451 A1 | 12/1991 |
| EP | 0 780 493 | 6/1997 |
| JP | 58-73781 A * | 5/1983 ............. C25B/9/00 |
| WO | WO 95/07375 | 3/1995 |

OTHER PUBLICATIONS

José González–García, et al. "Hydrodynamic Behavior of a Filter–Press Electrochemical Reactor with Carbon Felt As a Three–Dimensional Electrode." Ind. Eng. Chem. Res. 37, 1998, pp. 4501–4511.

Karsten Danielmeier, et al. "Electrochemical Oxidation of Chiral 5–Substituted 2–Oxazolidinones: A Key Building Block for Dichiral β–Amino Alcohols." Tetrahedron, 52, 1996, pp. 9743–9754.

M.D. Birkett, et al. "An Experimental Study of a Pilot–Scale Undivided and Quasi–Undivided Electrochemical Reactor." Electrochimica Acta. vol. 27, No. 2, 1982 pp. 263–268.

* cited by examiner

Primary Examiner—Roy King
Assistant Examiner—Harry D. Wilkins, III
(74) Attorney, Agent, or Firm—Oblon, Spviak, McClelland, Maier & Neustadt, P.C.

(57) ABSTRACT

Electrolysis cell consisting of 2 monopolar electrodes and one or more intermediate bipolar electrodes, where

Figure 1:
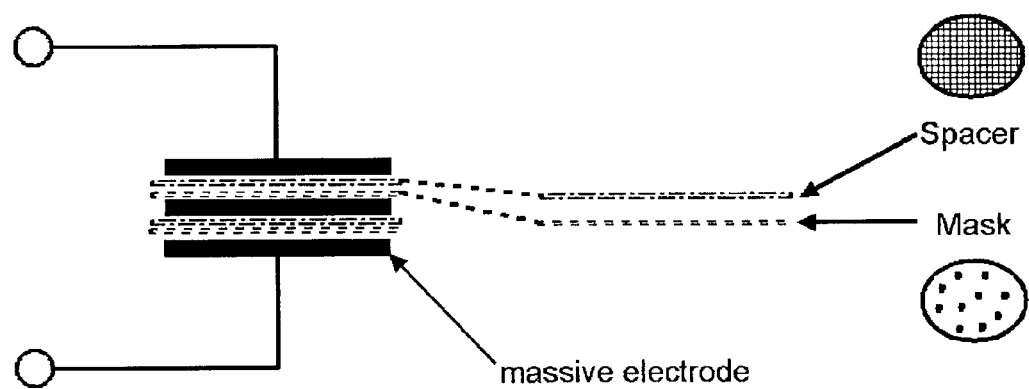

- the one monopolar electrode and the parts of the bipolar electrodes charged in the same sense thereto together form the working electrode and the other monopolar electrode and the parts of the bipolar electrodes charged in the same sense thereto together form the counter electrode
- the space between counter and working electrode is undivided
- the surface of the counter electrode consists of electrochemically active and inactive parts
- the sum of the electrochemically active parts of the surface of the counter electrode is smaller by a large amount than that of the electrochemically active parts of the surface of the working electrode.

17 Claims, 3 Drawing Sheets

BIPOLAR QUASI-DIVIDED ELECTROLYSIS CELLS

The present invention relates to an electrolysis cell consisting of 2 monopolar electrodes and one or more intermediate bipolar electrodes, where the one monopolar electrode and the parts of the bipolar electrodes charged in the same sense thereto together form the working electrode and the other monopolar electrode and the parts of the bipolar electrodes charged in the same sense thereto together form the counter electrode the space between counter and working electrode is undivided the surface of the counter electrode consists of electrochemically active and inactive parts the sum of the electrochemically active parts of the surface of the counter electrode is smaller by a large amount than that of the electrochemically active parts of the surface of the working electrode.

The invention furthermore relates to processes for the preparation of organic and inorganic compounds using the abovementioned electrolysis cells, in particular the preparation of di($C_1$- to $C_6$-alkyl) azodicarboxylates.

Electrolysis cells are employed in modern chemistry in a variety of shapes for a multiplicity of tasks. A general survey on the possibilities of construction of electrolysis cells is found, for example in D. Pletcher, F. Walsh, Industrial Electrochemistry, 2nd Edition, 1990, London 60 ff. The article by D. Degner, Topics in Current Chemistry, 148, 1 ff, 1988 offers a general survey on industrial, electrochemical processes. A frequently used and also industrially employed form of electrolysis cells is the stacked plate cell or capillary gap cell (cf. Ullmann's Encyclopedia of Industrial Chemistry, sixth Edition, 2000 Electronic Release, Chapter 5.4.3.2. "Cell Design"). Frequently, in the arrangement of the capillary gap cell, the electrodes and corresponding separating elements are arranged like a filter press and separated by spacer media such as spacers or diaphragms. A so-called undivided cell usually comprises only one electrolyte phase, a divided cell has two or more phases of this type. As a rule, the phases adjacent to the electrodes are liquid. However, 'solid electrolytes' such as ion exchange membranes can also be employed as electrolyte phases. If the electrode here is applied directly to the ion exchange membrane, e.g. in the form of an electrocatalytic and finely porous layer, contacts are additionally necessary which, on the one hand, have to be designed as current collectors, on the other hand as substance transport promoters. The individual electrodes can be connected in parallel (monopolar) or in series (bipolar).

In order to achieve a substance turnover in the electrolyte cells which is as high as possible, according to general teaching the electrolyte should be guided onto the electrodes in such a way that an optimum substance transport is achieved. In the case of liquid electrolytes, it is frequently proposed to allow the electrolyte liquid to flow parallel to the electrodes.

The space-time yield and the selectivity of the electrolysis also depend, besides the flow towards the electrodes, on the electrode materials used. These influence the durability, size and weight of the cell substantially.

In known stacked plate cells, the electrodes are mainly employed as massive plates, e.g. graphite disks.

These are also especially employed in the abovementioned industrial processes, such as in the synthesis of anisaldehyde dimethyl acetal in DE 2 848 397, tolyaldehyde dimethyl acetal in EP 129795 or for the preparation of α-hydroxymethyl ketals as described in EP 0460451.

Electrodes of this type have various disadvantages, which result from the massiveness of the material, e.g. the surface area, which is reduced compared with a porous material, and the decreased substance turnover accompanying it, which makes itself noticeable in lower current yields, higher weight and a greater space requirement. Furthermore, as a result of the bipolar switching of the massive electrodes, the anode corresponds in size to the area of the cathode.

In these cases, so-called three-dimensional electrodes offer a possibility of increasing the substance transport and thus a possibility of increasing the current yield.

Attempts at the optimization of the surface ratios are described, for example, in DE 19533773; a felt anode of large surface area was combined here with a flat cathode. In this case, electrodes differ in their surface area in that in the case of the counter electrode only the surface turned toward the electrolyte acts as an active surface, while the working electrode of the electrolyte can be flowed through. From the surface weights supplied by the manufacturers, surface ratios of working electrode to counter electrode of 1.2 to 2.4 can be calculated for the felts employed.

Montiel et al. (Ind. Eng. Chem. Res. 1998, 37 (11), 4501-11) likewise describe the use of graphite felts in a filter press in order to enlarge the surface area of the working electrode.

Often, however, it can occur that the anode space and cathode space have to be separated; this is preferably the case if chemical side reactions or back reactions are to be excluded or if subsequent substance separations are to be simplified. This can furthermore be the case if a substance is both readily oxidizable and reducible, so that an 'electron shuttle process' is present. If no separation of anode and cathode space is performed, the amount of charge used increases and undesired side reactions may occur.

An example of an reaction which, because of side reactions/back reactions, hitherto had to be run in a divided cell is the oxidation described, for example, in FR 02043109 (DT 2016764) of hydrazodicarboxylic acid amides or hydrazodicarboxylic acid esters to the corresponding azo compounds. The separation of the electrolysis circulations is achieved here by a diaphragm or a membrane.

In this case, as a rule, divided cells are used. A plane-parallel electrode arrangement or candle-shaped electrodes are frequently used here. As the separation medium, ion exchange membranes, microporous membranes, diaphragms, filter fabric made of nonelectron-conducting materials, glass frits and also porous ceramics may be employed. The construction of such cells, however, is relatively complicated. Ion exchange membranes, in particular cation exchange membranes, are furthermore used, preferably those which consist of a copolymer of tetrafluoroethylene and a perfluorinated monomer which contains sulfo groups. These conductive membranes are commercially obtainable under the trade names Nafion® (E. T. DuPont de Nemours and Company) and Gore Select® (W. L. Gore & Associates, Inc.).

The use of these membranes often comes up against limiting factors as soon as operations are carried out in organic solvents. The membranes swell and are not suitable for further use in electrolysis.

As an alternative to the divided cells just described, 'quasi-divided or pseudo-divided cells' can also be employed here which hitherto were especially used on the laboratory scale. The principle which underlies this type of cell is that the working electrode has a markedly greater surface area than the corresponding counter electrode.

Investigations to this end were carried out, for example, by Hamzah and Kuhn (Chem.-Ing.-Tech. 52, (1980), 762–763). The influence of surface ratios of anode and cathode on the formation of hypochlorite from chloride was determined, the surface ratios being varied from 0.76/1 to 1.8 to 1.

An electrolysis cell was described by E. Steckhan et al. Tetrahedron, 52, 1996, 9743–9754 in which a wire electrode is combined with a flat or three-dimensional electrode which can be flowed through, also in the form of a cylindrical arrangement.

In Electrochimica Acta 27, 1982, 263–268, Birkett et al. describe the use of a monopolar plate and frame cell, which has considerable area differences between anode and cathode. Birkett et al. achieved the area difference by spraying electrodes with lacquer and thus insulating the surface by means of a nonconductive layer. Alternatively to this, the surface area of a massive two-dimensional electrode was markedly reduced by covering with a thick polypropylene fabric. The maximum area difference was 2.7 $cm^2$ for the counter electrode and 200 $cm^2$ for the working electrode. The disadvantages here are the monopolar procedure and the comparatively high voltages which these systems exhibit.

An industrially relevant quasi-divided cell is described in WO 95/07375 from EA technology. Here, a graphite felt of large surface area is employed as a cathode, which is placed opposite a DSA extended metal electrode as an anode.

The disadvantage in these constructions, however, is that on account of the specific spatial arrangement of working and counter electrode, the reactions have an unfavorable space-time yield.

The technical object thus consisted in making available a type of cell which is relatively simply constructed in comparison with divided cells, in which the specific preparation of chemical compounds with high yield, based on the amount of charge employed and amount of starting compounds, and high selectivity were possible, is possible with high space-time yield.

The construction of the electrolysis cell according to the invention is in general carried out in the manner of a stacked plate cell or capillary gap cell. Here, the bipolar electrodes, in particular, are arranged parallel to one another in the form of flat elements such as plates, sheets, disks, webs, foils or other flat structures.

The surface of the bipolar electrode having the one polarity forms the working electrode, the surface having the other polarity forming the counter electrode. In this case, the electrochemically active part of the surface of the counter electrode is smaller by a large amount than the electrochemically active part of the surface of the working electrode. Preferably, the ratio of active parts of the surface of the working electrode to active parts of the surface of the counter electrode is 1.5:1 to 25:1, preferably 2:1 to 10:1. Here, according to the invention, active parts of the surface of the counter electrode are inactivated. This means that on these parts of the surface, an electrochemical reaction can virtually no longer take place. The ratio of activated surface parts to inactive surface parts is in general 0.01:1 (residual area: 1%) to 0.5:1 (50%), preferably 0.03:1 (3%) to 0.3:1 (30%), particularly preferably 0.05 (5%):1 to 0.2 (20%):1.

Suitable materials for the working electrode are, for example, massive materials such as massive graphite, graphite board and in particular materials which can be flowed through by the electrolytes, such as graphite felt plate, carbon felt plate, fabric having a carbon-covered electrolyte contact surface, carbon fabric, carbon nets, other porous solids made of carbon, other porous materials which do not consist of carbon, which are filled with carbon or are covered with carbon on the electrolyte contact surface, and also porous materials, e.g. metal sponges. Such materials are described, for example, in DE-A-19533773.

The materials which can be flowed through are preferably employed, since these, based on the space requirement needed by them, have a particularly high electrochemically active surface area.

Suitable materials for the counter electrode are, for example, massive graphite, graphite board, massive metal or metal oxide, massive graphite, covered on the electrolyte contact surface with a thin layer of metal, e.g. metal foil, massive graphite, covered on the electrolyte contact surface with a cation or anion exchange membrane, which are optionally coated with a catalyst.

In the case where metals or metal oxides are used, platinum, iron/iron oxide, nickel/nickel oxide, copper, silver, cadmium or lead/lead dioxide are particularly suitable.

Metals, in particular metal foils, are particularly preferred if the counter electrode is connected as a cathode, since in such cases the hydrogen overvoltage is reduced to a minimum. By means of this, an undesired back reaction and consequently electron shuttling can be avoided and, instead of this, hydrogen is formed.

Suitable ion exchange membranes (electrically conductive films) are particularly polymers processed to give films, such as polyethylene, polyacrylates, polysulfone and perfluorinated polymers having negatively charged groups such as carboxylate and sulfonate groups (cation exchange membrane) or positively charged groups such as protonated or quaternary amino groups (anion exchange membrane). Suitable cation exchange polymers are, for example, anionic perfluorinated polymers which carry sulfonate groups. Such films are commercially obtainable, for example, under the trade names Nafion® (DuPont de Nemours and Company) and Gore Select® (W. L. Gore & Associates). Suitable catalysts with which the ion exchange membranes can be coated are platinum, palladium or alternatively nickel powder and active carbon, and also mixtures thereof.

The bipolar electrodes customarily consist either of surface elements made of a single one of the abovementioned materials, provided the corresponding material is listed in the two above lists for working and counter electrode materials.

The bipolar electrodes can furthermore be composed of 2 surface elements made of 2 or more different materials, of which each is picked out from one of the above lists for working and counter electrode materials. In this case, the surface elements are in direct contact with one another, i.e. are of sandwich-like composition.

The combination is particularly preferred in which a massive material forms the counter electrode and a material which can be flowed through forms the working electrode.

Parts of the counter electrode are generally inactivated by covering appropriate active parts of the surface with a lacquer or a film of nonconducting material such as Teflon, polyethylene or polypropylene (called a "mask" below).

Preferably, perforated plastic films are used as masks. The holes in said electrically nonconductive plastic film are applied such that the surface area of the electrode is reduced to values of 1–50%, furthermore preferably to 3–30% and particularly preferably to 5–20%. The size of the holes is in general dimensioned such that the mean value of the maximum distances between 2 points in a hole is 0.05 mm to 50 mm, particularly preferably 2 mm to 20 mm and especially preferably 3 mm to 10 mm. In general, the holes are randomly distributed. The form of the still active surface area, however, is not restricted to holes. It can likewise be achieved, for example, by means of strips, spirally shaped cut films or other types of covering form; only a flat covering which decisively decreases the size of the surface area of the counter electrode in comparison with the working electrode is important.

The thickness of the film is in general 0.1 µ to 5 mm.

As is known, the bipolar electrolysis cells having parallel surface elements as bipolar electrodes are in general operated such that the electrolyte continuously flows parallel to the electrodes and a flow along the potential drop is suppressed if possible. This undesired flow can be particularly effectively prevented in that part of the bipolar electrodes is a layer which is penetrable with difficulty or impenetrable for the electrolytes. This layer is, for example, metal foil, preferably graphite board. These measures can be taken independently of the composition of the electrolyte.

For reasons of optimization of the space-time yield, the space between the working electrode and counter electrode is chosen to be as small as possible and the bipolar electrodes are preferably stacked on one another. In such stacked electrolysis cells, counter electrode and working electrode which belong to 2 opposite bipolar stacked electrodes, but are only brought closer in so far that it is ensured that a) the active parts of the counter electrode and the working electrode do not touch, in order to prevent a short circuit and b) the abovementioned substance transport of the electrolyte is still possible.

The maximum approach and in particular stacking of the bipolar electrodes on fulfilling the abovementioned requirements can be achieved using 2 different implementation variants:

On the one hand, it is possible to fill the space between working and counter electrode partially with a spacer layer of nonconducting material, which is arranged such that this space can be flowed through by the electrolyte, but a direct coming into contact of the surfaces of working and counter electrode is prevented (called spacer below). The working electrode can in this case be flowable through or not flowable through. The second embodiment is illustrated in FIG. 1.

In particular when using massive electrodes, the spacer can be applied directly to these, e.g. in the form of knobs. However, the use of nets or fabrics, webs of plastics, which, as forms of fabric, are woven, knitted, expanded and stamped or linked by means of other forms to give fabrics is preferred, the nature of the fabric being uncritical; it only has to be an electrical nonconductor, such as, for example, polyethylene, polypropylene or Teflon.

In this implementation variant, all aforementioned electrode materials can be used.

Figure 2:
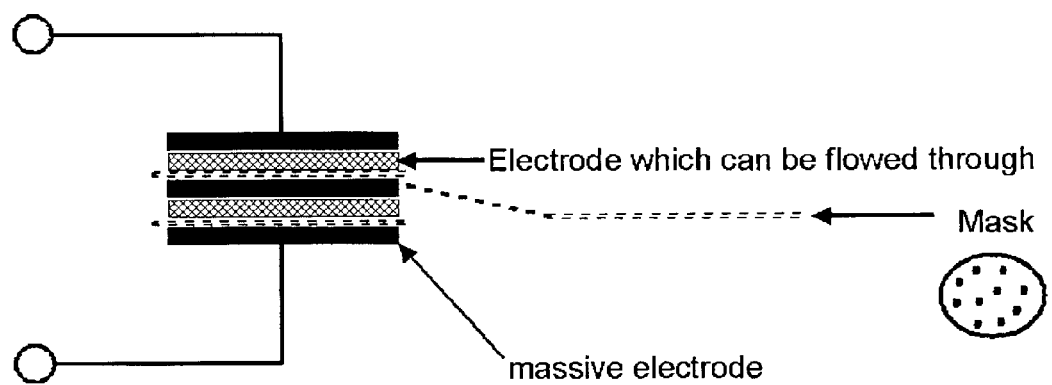

According to a second implementation variant (cf. FIG. 2), no spacer is used.

In this case, the surface of the working electrode preferably lies directly on the surface of the mask of the opposite counter electrode. In this case, a space exists between working and counter electrode virtually only in the positions at which the mask does not cover the counter electrode. In order to ensure in this case that in the stacked electrodes substance transport is still possible parallel to the bipolar electrodes, a material which can be flowed through by the electrolyte must be chosen as the working electrode.

However, so that it is ensured that the material which can be flowed through, which forms the working electrode, is not pressed through the open spaces of the mask onto the counter electrode and thus causes a short circuit, it is recommended to use as a mask a perforated film in which the maximum distance between 2 points in a hole is 0.05 mm to 5 mm, preferably 0.1 mm to 3 mm, particularly preferably 0.1 to 0.5 mm. Preferably, the film has a thickness of 0.1 µm to 3 mm, preferably 0.5 mm to 1.5 mm.

Figure 3:
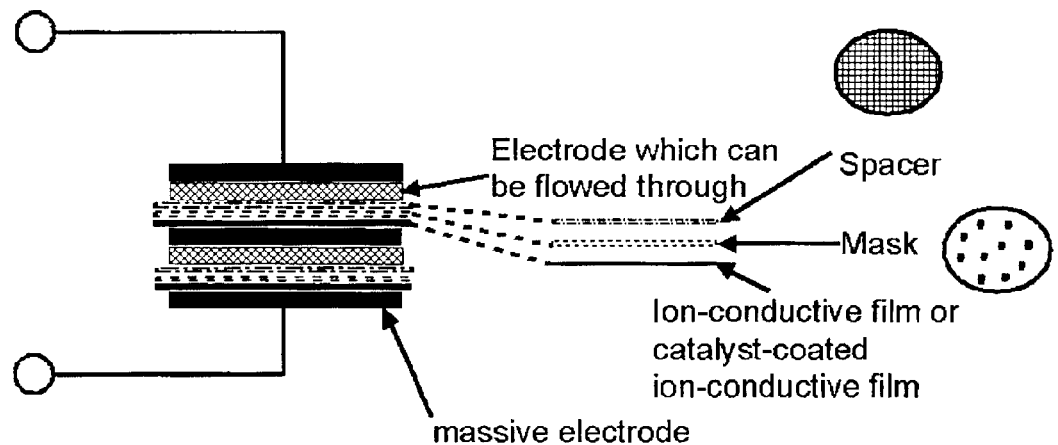

In the case of the use of electrodes coated with ion exchange membranes, the construction shown in FIG. 3 is usually used.

In principle, the working electrode can in each case be the anode or cathode, from which it results that both the cathode and the anode can function as the counter electrode, which is restricted in its electrochemically active surface area.

By means of the reduction of the electrode surface area with the aid of an electrical nonconductor, the voltage of the system can be increased from about 3–6 V/gap up to 20–30 V/gap. This has the consequence that a large part of the electrical energy is lost in the form of heat. As a counter measure, the conductivity of the electrolytes can be increased, but only to the extent that the bipolarity of the graphite disks can still be maintained. As a reference point, a doubling up to quintupling of the concentration of the electrolytes can be assumed.

The current densities in the process according to the invention are in general approximately 100 A/m$^2$ to approximately 10,000 A/m$^2$, preferably approximately 300 A/m$^2$ to 5000 A/m$^2$. These values relate to the area of the working electrode.

The process according to the invention is in general carried out at temperatures from –10° C. up to the boiling point of the solvent used in each case, temperatures from 5 to 100° C., in particular 10 to 60° C., being preferred.

Depending on the compound to be reacted, the process according to the invention can be carried out in acidic medium, i.e. at a pH which is under 7, in neutral medium, i.e. at a pH of approximately 7 and in basic medium, i.e. at a pH which is over 7.

In particular, the electrochemical reaction according to the invention can be carried out either continuously or batchwise.

In general, the electrochemical reaction according to the invention is performed in the presence of an auxiliary electrolyte. In addition to the adjustment of the conductivity of the electrolysis solution, the auxiliary electrolyte occasionally also serves to control the selectivity of the reaction.

As a rule, the auxiliary electrolyte is contained in a concentration of approximately 0.1 to approximately 10, preferably approximately 0.2 to approximately 3, % by weight, in each case based on the reaction mixture. Suitable auxiliary electrolytes are protonic acids, such as, for example, organic acids, it being possible to mention methanesulfonic acid, benzenesulfonic acid or toluenesulfonic acid, and mineral acids, such as, for example, sulfuric acid, hydrochloric, hydrobromic and hydriodic acid and phosphoric acid. Neutral salts can furthermore also be used as auxiliary electrolytes. Possible cations in this case are metal cations of lithium, sodium, potassium but also tetraalkylammonium cations, such as, for example, tetramethylammonium, tetraethylammonium, tetrabutylammonium and dibutyldimethylammonium. Anions which may be mentioned are: fluoride, tetrafluoroborate, sulfonates, such as, for example, methylsulfonate, benzenesulfonate, toluenesulfonate, sulfates, such as, for example, sulfate, methylsulfate, ethylsulfate, phosphates, such as, for example, methylphosphate, dimethylphosphate, diphenylphosphate, hexafluorophosphate, phosphonates, such as, for example, methylphosphonate methyl esters and phenylphosphonate methyl esters, but also the halides chloride, bromide and iodide.

Basic compounds such as, for example, alkali metal or alkaline earth metal hydroxides, carbonates, hydrogencarbonates and alkoxides can furthermore also be employed, the alkoxide ions methoxide, ethoxide, butoxide and isopropoxide preferably being employed.

Possible cations in these basic compounds are in turn the cations mentioned above.

Additionally preferably, the auxiliary electrolyte employed can also be an electrochemically active agent, thus bromine which is formed, for example, from hydrobromic acid can be the electrochemically active oxidant which carries out the actual reaction with the substrate.

In principle, suitable solvents are all protic solvents, i.e. solvents which contain and can release protons and/or can form hydrogen bonds, such as, for example, water, alcohols, amines, carboxylic acids etc., if appropriate as a mixture with aprotic polar solvents such as, for example, THF, 1,2-dimethoxyethane and dioxane in the process according to the invention.

Because of the conductivity which has to be maintained, lower alcohols such as methanol, ethanol, isopropanol, n-propanol, n-butanol, sec-butanol, tert-butanol, ethers, such as, for example, diethyl ether, 1,2-dimethoxyethane, furan, THF, acetonitrile and dimethylformamide are preferably employed here, preferably a mixture of these solvents or furthermore preferably water as a mixture with these solvents in all possible mixing ratios.

Alternatively to the abovementioned alcohols, their carboxylic acids or amides can also be used. Carboxylic acids preferably employed are formic acid, acetic acid, propionic acid and longer-chain branched and unbranched carboxylic acids, furthermore also sulfuric acid, hydrochloric acid, hydrobromic acid and hydriodic acid.

The electrolysis cell according to the invention is fundamentally suitable for the preparation of any desired organic and inorganic compounds which can be prepared electrochemically. Preferably, it is employed for the preparation of those compounds in which, in customary undivided cells on the counter electrode, they are either converted back to the starting material or are converted into other undesired products. The electrolysis cell is furthermore suitable for converting redox mediators into the desired oxidation state, in which these can react with a substrate with the change of their oxidation state.

Since in the following reactions the procedure according to the process of the prior art is associated with at least one of the disadvantages explained, these can be carried out with advantage in the electrolysis cell according to the invention:

The reactions which are taken back to the starting material in the undivided procedure include the oxidation of hydrazines to diazo compounds, the oxidation of hydroquinones to quinones and conversely, the oxidation of organic iodo compounds to the iodoso compounds and occasionally also to the bisacyloxyiodo compounds.

The reactions which lead to the destruction of the products formed in the undivided procedure include the reaction of aldehydes to give carboxylic acids which hydrodimerize in a competing reaction or can be reduced to the alcohol. Ketones which are reacted to give α-hydroxyketals can likewise hydrodimerize in a competing reaction or be reduced to the alcohol. In the α-oxidation of ketones to α-hydroxy-, or α-formyl-esters esters, such as, for example, the oxidation of acetophenone to phenylglyoxylic acid, hydrodimerization or reduction can likewise occur as a side reaction.

Furthermore, in the reaction of hydroxyamines to give amines, a competing reaction to give oximes and further decomposition products is observed. Aromatic nitro compounds which are reacted to give aniline derivatives exhibit, as competing reactions, decomposition and polymerization reactions. If α-nitrobenzoic acids are reacted to give the corresponding benzoxazolinones, free-radical decomposition reactions occur. In the reaction of hydrazines, control of the reaction is necessary in as much as that both the azo compound (see above), and hydrazones or a hydrazine cleavage can be the desired reaction. In the reduction of oxalic acid to glyoxylic acid, the further oxidation of the oxalic acid to $CO_2$ can be prevented using this process. In the case of the dehalogenation of compounds, the polyhalogenation by liberated halogen should be avoided in this manner.

In the case of electroenzymatic reactions, the aim is to avoid, if appropriate, a decomposition of the enzyme on the corresponding electrode.

The third case, the regeneration of mediators in this quasi-divided cell, includes inorganic systems, for example Ce (III/IV), Mn (II/III), Cr (II/III); Cr (III/VI); Ti (II/III); V (II/III); V (III/IV); V (IV/V); Ag (I/II); $AgO^+/AgO^-$; Cu (I/II); Sn (II/IV); Co (II/III); Mn (II/III); Mn (II/IV); Mn (II/VI); Os (IV/VIII); Os (III/IV); Os (IV/VI); $Br_2/Br^-$/ $BrO_3^-$; $I_2$, $I^-$, $IO_3^-$, or alternatively organic mediators such as ABTS, $NAD^+$/NADH, $NADP^+$/NADPH, TEMPO, viologens, it also being possible for the systems indicated to be metal complexes with various ligands or alternatively solvent ligands.

The electrolysis cell according to the invention is particularly suitable for the preparation of azo compounds, in particular of di($C_1$- to $C_6$-alkyl) azodicarboxylates from di($C_1$- to $C_6$-alkyl) hydrazodicarboxylates, diethyl, diisopropyl or di-tert-butyl azodicarboxylates being very particularly preferred.

Because of the low stability of the aforementioned azo compounds, an integrated overall process having an integrated working-up process is necessary here.

J. E. Herweh et al., in J. Org. Chem. 39, 1974, 786–793 und A. S. Prakash in J. Chem. Soc. Perkin II, 1975, 1, 46–50; report the thermal decomposition of diazoamides; in the case of the diazoesters, comparable by-products are observed in the materials removed from the electrolysis even at room temperature in the presence of water. In this connection, a decomposition reaction of azodicarboxylic acid esters in water-containing media can be explained in the analogy of water to alcohols (F. Yoneda et al. describe the oxidation of alcohols to the corresponding ketones by means of azodicarboxylic acid esters in Am. Soc. 1966, 88, 2328–2329).

The lacking stability of the azodicarboxylic acids is also to be observed in their purification, this applies in particular when, in addition to the direct synthesis of the diazoesters from the corresponding hydrazine, an electrochemical recycling of used azo ester is carried out.

The procedure is customarily carried out in the following way in order to avoid decomposition reactions:

The hydrazinedicarboxylic acid ester is dissolved in the electrolyte and reacted in a variant of the quasi-divided capillary gap cell described above. Inert organic aprotic solvents such as ether are preferred, which are optionally employed as a mixture with protic solvents. If water, solvent mixtures with water or alcohols oxidizable in the C1 position are employed as reaction medium in the electrolysis, the azo ester formed should be removed rapidly from the reaction medium, since both water and alcohols lead to the decomposition of the azo ester (see above). The material removed from the electrolysis is immediately added to an inert, aprotic organic medium such as, for example, diethyl ether, methyl tert-butyl ether, ethyl acetate, alkanes, such as, for example, pentane, n- or i-hexane, n- or i-heptane, cyclohexane, methylcyclohexane, toluene, dichloromethane, inter alia, which is not miscible with water. The resulting azo ester is thus extracted into the organic phase, in which it is stable and can be further processed according to customary methods after separating off the aqueous phase.

<In the diazo esters are used in the Mitsunobu reaction (O. Mitsunobu in Bull. Chem. Soc. Jpn. 1967, 40, 4235–4238 and Synthesis 1981, 1–28) the hydrazodicarboxylic acid esters to be reacted are present in the form of a mixture with triphenylphosphine oxide. In addition to the regeneration of the hydrazodicarboxylic acid ester, in order to achieve a separation thereof from triphenylphosphine oxide, an advantageous procedure is used in which

- an organic/aqueous solution, comprising hydrazodicarboxylic acid ester and triphenylphosphine oxide is first subjected to an electrolysis and in the course of this the hydrazodicarboxylic acid ester is reacted to give azodicarboxylic acid ester
- the reaction mixture is extracted with a nonpolar solvent in which the triphenylphosphine oxide only dissolves with difficulty, e.g. alkanes, such as pentane, n- or i-hexane, n- or i-heptane, cyclohexane, methylcyclohexane, or aromatics such as toluene.
- the aqueous phase is extracted with an organic solvent which is essentially insoluble in water and in which triphenylphosphine oxide dissolves readily, e.g. diethyl ether, methyl tert-butyl ether, ethyl acetate or dichloromethane
- the azodicarboxylic acid ester and the triphenylphosphine oxide are isolated from the two extracts according to customary methods.

EXPERIMENTAL SECTION

Oxidation of Hydrazodiisopropylcarboxylic Acid Esters to Diisopropyl Azodicarboxylates Comparison Example 1

Both Massive

The plate stack consisted of two massive annular disks of graphite, which are arranged at a distance of 1 mm from one another. The electrolyte consisted of 510 g of ethylene glycol dimethyl ether, 70 g of water, 14.8 g of concentrated sulfuric acid and 35 g of diisopropyl hydrazodicarboxylate and 81.7 g of triphenylphosphine oxide.

The electrolysis was carried out at a temperature of 6° C. and with a current density of 34 mA/cm$^2$. After 4F, the conversion is 42%, after a further 2F a conversion of 50% is achieved; the system is in a equilibrium between product formation and back reaction to the starting material.

Comparison Example 2

Procedure in a Divided Plate and Frame Cell of the Flow-Through Type

| Membrane: | Nafion 324 |
|---|---|
| Anode: | Massive graphite 35 cm$^2$ |
| Cathode: | Stainless steel (V2A): 35 cm$^2$ |

The catholyte consisted of 73.5 g of ethylene glycol dimethyl ether, 73.5 g of water and 3.1 g of concentrated sulfuric acid.

The anolyte consisted of a mixture of 88.1 g of ethylene glycol dimethyl ether, 33.8 g of water, 3.1 g of concentrated sulfuric acid and 7.5 g of diisopropyl hydrazodicarboxylate and 17.5 g of triphenylphosphine oxide.

The reaction was carried out as follows: firstly, the two cell compartments were filled and cooled to 10° C. The current density of the electrolysis is 17 mA/cm$^2$. After an applied amount of charge of 4F, the conversion is 84%. After working up the material removed from the electrolysis, a yield of 75% of diisopropyl azodicarboxylate (5.6 g) is obtained.

Comparison Example 3

Procedure in a Divided Plate and Frame Cell of the Flow-Through Type

| Membrane: | Nafion 324 |
|---|---|
| Anode: | Graphite 35 cm$^2$ |
| Cathode: | Stainless steel (V2A): 35 cm$^2$ |

The catholyte consisted of 73.5 g of ethylene glycol dimethyl ether, 73.5 g of water and 3.1 g of concentrated sulfuric acid.

The anolyte consisted of a mixture of 86.6 g of ethylene glycol dimethyl ether, 33.8 g of water, 3.1 g of concentrated sulfuric acid, 1.5 g of sodium bromide, 7.5 g of diisopropyl hydrazodicarboxylate and 17.5 g of triphenylphosphine oxide.

The reaction was carried out as follows: firstly, the two cell compartments were filled and cooled to 10° C. The current density of the electrolysis is 17 mA/cm$^2$. After an applied amount of charge of 4F, the conversion is 95%. After working up the material removed from the electrolysis, a yield of 92% of diisopropyl azodicarboxylate (6.9 g) is obtained.

Example 1

Undivided in DME/Water-Felt Anodes/Graphite Cathodes and With PTFE-Covered Cathode (2.5% Residual Electrode Area) of thick felt The plate stack consisted of two massive annular disks of graphite and a graphite felt of the type RVG 2003 having a thickness of 6 mm. The spacer used was a filter net of polypropylene. The cathode, which consisted of a massive graphite electrode, was covered with a Teflon film which, by means of holes of a diameter of 1.5 mm, reduced the electrode area to 2.5% of the originally employed area. The electrolyte consisted of 383.9 g of ethylene glycol dimethyl ether, 210 g of water, 14.6 g of concentrated sulfuric acid, 7 g of sodium bromide and 35 g of diisopropyl hydrazodicarboxylate and 47.4 g of triphenylphosphine oxide.

The electrolysis was carried out at a temperature of 20° C. and with a current density of 34 mA/cm$^2$. After 4F, complete conversion is achieved and after working up, a yield of 84% of diisopropyl azodicarboxylate (29.06 g) is obtained.

Example 2

Thinner Felt 2.5%

A change of the anode surface to a thinner felt electrode results in a decreased conversion and a decreased selectivity.

The plate stack consisted of two massive annular disks of graphite and a graphite felt of the type KFD 2 having a thickness of 2 mm. The spacer used was a filter net of polypropylene. The cathode, which consisted of a massive graphite electrode, was covered with a Teflon film which, by means of holes of a diameter of 1.5 mm, reduced the electrode area to 2.5% of the originally employed area. The electrolyte consisted of 436.4 g of ethylene glycol dimethyl ether, 157.5 g of water, 14.6 g of concentrated sulfuric acid, 7 g of sodium bromide and 35 g of diisopropyl hydrazodicarboxylate and 47.4 g of triphenylphosphine oxide.

The electrolysis was carried out at a temperature of 20° C. and with a current density of 34 mA/cm$^2$. After 4F, the conversion is 79%. After working up, a yield of 63% of diisopropyl azodicarboxylate (21.81 g) is obtained.

Example 3

Undivided in DME/Water-Felt Anodes/Graphite Cathodes and With a PTFE-Covered Cathode (10% Residual Electrode Area) 1 Gap HBr The plate stack consisted of two massive annular disks of graphite and a graphite felt of the type Carbone RVG 2003 having a thickness of 6 mm. The spacer used was a filter net of polypropylene. The cathode, which consisted of a massive graphite electrode, was covered with a Teflon film which, by means of holes of a diameter of 3.0 mm, reduced the electrode area to 10% of the originally employed area. The electrolyte consisted of 428.5 g of ethylene glycol dimethyl ether, 157.5 g of water, 14.6 g of concentrated sulfuric acid, 14.9 g of 47% strength hydrobromic acid and 35 g of diisopropyl hydrazodicarboxylate and 47.4 g of triphenylphosphine oxide.

The electrolysis was carried out at a temperature of 20° C. and with a current density of 34 mA/cm$^2$. After 4F, the conversion was 99%. After working up, a yield of 90% of diisopropyl azodicarboxylate (31.3 g) is obtained.

Example 4

The plate stack consisted of four massive annular disks of graphite and three graphite felts of the type Carbone RVG 2003 having a thickness of 6 mm. The spacer used was a filter net of polypropylene. The cathodes, which consisted of a massive graphite electrode, were covered with a Teflon film which, by means of holes of a diameter of 3.0 mm, reduced the electrode area to 10% of the originally employed area. The electrolyte consisted of 428.5 g of ethylene glycol dimethyl ether, 157.5 g of water, 14.6 g of concentrated sulfuric acid, 14.9 g of 47% strength hydrobromic acid and 35 g of diisopropyl hydrazodicarboxylate and 47.4 g of triphenylphosphine oxide.

The electrolysis was carried out at a temperature of 20° C. and with a current density of 34 mA/cm$^2$. After 5F, the conversion is 100%. After working up, a yield of 90% of diisopropyl azodicarboxylate (31.4 g) is obtained.

Example 5

Undivided in DME/Water-Felt Anodes/Graphite Cathodes and Having a PTFE-Covered Cathode (20% Residual Electrode Area)

The plate stack consisted of two massive annular disks of graphite and a graphite felt of the type Carbone RVG 2003 having a thickness of 6 mm. The spacer used was a filter net of polypropylene. The cathodes, which consisted of a massive graphite electrode, were covered with a Teflon film which, by means of holes of a diameter of 3.0 mm, reduced the electrode area to 20% of the originally employed area. The electrolyte consisted of 428.5 g of ethylene glycol dimethyl ether, 157.5 g of water, 14.6 g of concentrated sulfuric acid, 14.9 g of 47% strength hydrobromic acid and 35 g of diisopropyl hydrazodicarboxylate and 47.4 g of triphenylphosphine oxide.

The electrolysis was carried out at a temperature of 20° C. and with a current density of 34 mA/cm$^2$. After 4F, the conversion is only 78%. After working up, a yield of 76% of diisopropyl azodicarboxylate (22.6 g) is obtained; if in a repeat experiment an amount of charge of 6F is employed, full conversion can likewise be achieved (yield then 28.27 g: 81%. At 4F the conversion is only 78%. After working up a yield of 76% of diisopropyl azodicarboxylate is obtained).

Example 6

Undivided in DME/Water-Felt Anodes/Graphite Cathodes and With a PTFE-Covered Cathode (15% Residual Electrode Area)

The plate stack consisted of two massive annular disks of graphite and a graphite felt of the type Carbone RVG 2003 having a thickness of 6 mm. The spacer used was a filter net of polypropylene. The cathodes, which consisted of a massive graphite electrode, were covered with a Teflon film which, by means of holes of a diameter of 3.0 mm, reduced the electrode area to 15% of the originally employed area. The electrolyte consisted of 428.5 g of ethylene glycol dimethyl ether, 157.5 g of water, 14.6 g of concentrated sulfuric acid, 14.9 g of 47% strength hydrobromic acid and 35 g of diisopropyl hydrazodicarboxylate and 47.4 g of triphenylphosphine oxide.

The electrolysis was carried out at a temperature of 20° C. and with a current density of 34 mA/cm$^2$. After 4F, the conversion is 80%; after 4.5F the conversion is 90%. After working up, a yield of 76% of diisopropyl azodicarboxylate (26.5 g) is obtained.

In the abovementioned experiments, comparable yields were obtained if dimethoxyethane was replaced by tert-butanol or tetrahydrofuran.

Working-up of an electrolysis diskharge from the oxidation of diisopropyl hydrazodicarboxylate, DIHD, to diisopropyl azodicarboxylate, DIAD:

82 g of the electrolysis diskharge from example 1 was diluted with 150 ml of water and the solution was then extracted with 90 ml of MTBE, and after washing a further three times with 40 ml of MTBE each time, the organic phases were combined and freed from the solvent.

The residue obtained on the rotary evaporator was washed by stirring in n-heptane and the precipitated triphenylphosphine oxide was separated off. The triphenylphosphine oxide thus obtained had a purity of 97%; the azodicarboxylic acid ester obtained had a purity of 75%.

Abbreviations:

ABTS:

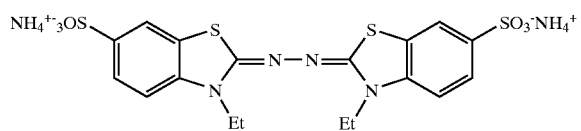

-continued

TEMPO:

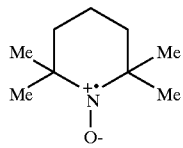

Viologen:

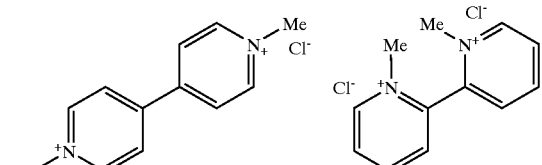

2,2'- and 4,4'-methylviologens

MTBE:

Methyl tert-butyl ether.

We claim:

1. An electrolysis cell comprising a first and second monopolar electrode and one or more intermediate bipolar electrodes, wherein
   the first monopolar electrode and the parts of the intermediate bipolar electrode charged in the same sense as the first monopolar electrode together form a working electrode and the second monopolar electrode and the parts of the bipolar electrodes charged in the same sense as the second monopolar electrode together form a counter electrode,
   the space between the counter and working electrode is undivided,
   the surface of the counter electrode comprises electrochemically active and inactive parts,
   the sum of the electrochemically active parts of the surface of the counter electrode is significantly smaller than the sum of the electrochemically active parts of the surface of the working electrode, and
   wherein the working electrode is porous.

2. An electrolysis cell as claimed in claim 1, wherein the monopolar and intermediate bipolar electrodes are present in the form of plates, sheets, discs, webs, foils or other flat structures and are arranged parallel to one another.

3. An electrolysis cell as claimed in claim 1, further comprising counter electrodes in which electrochemically inactive parts of the surface of the counter electrodes are produced by covering the corresponding active parts of the surface of the counter electrodes with an electrically nonconducting material.

4. A electrolysis cell as claimed in claim 3, wherein the covering is a perforated nonconducting plastic film having holes, and the covering is applied to the counter electrode on the electrolyte contact surface of the counter electrode.

5. An electrolysis cell as claimed in claim 4, wherein the size of the holes is such that the mean value of the maximum distance between 2 points in a hole is 0.05 to 50 mm.

6. An electrolysis cell as claimed in claim 5, wherein the holes are distributed randomly or according to a specific pattern.

7. An electrolysis cell as claimed in claim 3, wherein 1 to 75% of the total area of the counter electrodes is electrochemically active.

8. An electrolysis cell as claimed in claim 1, wherein the electrolysis cell is a stacked plate cell or capillary gap cell.

9. An electrolysis cell as claimed in claim 1, wherein the counter electrode is prepared from a material selected from the group consisting of: massive graphite, graphite board, massive metal, massive graphite coated on the electrolyte contact surface with a thin layer of metal foil, massive graphite coated on the electrolyte contact surface with a cation or anion exchange membrane which is optionally coated with a catalyst, and combinations thereof.

10. An electrolysis cell as claimed in claim 1, wherein the working electrode is prepared from a material selected from the group consisting of:
    massive graphite, graphite felt plate, carbon felt plate, fabric having a carbon-covered electrolyte contact surface, porous solid filled with carbon, porous metals, metal sponges, and combinations thereof.

11. An electrolysis cell as claimed in claim 1, wherein the space between the working and counter electrode is partly filled with a spacer layer of nonconducting material, and the spacer layer is arranged such that an electrolyte can flow through the space and wherein the surfaces of the working and counter electrode are prevented from coming into contact.

12. An electrolysis cell as claimed in claim 11, comprising the spacer layer in combination with a working electrode comprising a massive material which the electrolyte cannot flow through.

13. An electrolysis cell as claimed in claim 1, further comprising a counter electrode covered with a perforated plastic film having holes, and the size of the holes is such that the maximum distance between 2 points in a hole is 0.05 mm to 50 mm.

14. An electrolysis cell as claimed in claim 1, further comprising a counter electrode covered with a perforated plastic film which is 0.1 mm to 5 mm thick.

15. An electrolysis cell as claimed in claim 1, wherein the distance between the counter and working electrode is 0.2–5 mm.

16. An electrolysis cell as claimed in claim 4, wherein
    the electrolyte can flow through the working electrode,
    the counter electrode is covered with a perforated plastic film having holes, and the size of the holes is such that the maximum distance between 2 points in a hole is 0.05 mm to 5 mm, and the thickness, of the perforated plastic film is from 0.1 mm to 3 mm, and
    the working electrode is in contact with the perforated plastic film.

17. An electrolysis cell as claimed in claim 15, wherein the distance between the counter and working electrode is 0.5–1.5 mm.

* * * * *